US009582890B2

United States Patent
Gupta et al.

(10) Patent No.: US 9,582,890 B2
(45) Date of Patent: Feb. 28, 2017

(54) SUPERPIXEL-BASED IMAGE SEGMENTATION USING SHADING AND ALBEDO DECOMPOSITION

(71) Applicants: Mithun Das Gupta, Bangalore (IN); Srinidhi Srinivasa, Bangalore (IN)

(72) Inventors: Mithun Das Gupta, Bangalore (IN); Srinidhi Srinivasa, Bangalore (IN)

(73) Assignee: Ricoh Company, LTD., Tokyo (JP)

( * ) Notice: Subject to any disclaimer, the term of this patent is extended or adjusted under 35 U.S.C. 154(b) by 107 days.

(21) Appl. No.: 14/491,890

(22) Filed: Sep. 19, 2014

(65) Prior Publication Data

US 2015/0327766 A1    Nov. 19, 2015

Related U.S. Application Data

(60) Provisional application No. 62/000,255, filed on May 19, 2014.

(51) Int. Cl.
| | | |
|---|---|---|
| *G06T 7/00* | (2006.01) | |
| *A61B 5/00* | (2006.01) | |
| *G06T 7/40* | (2006.01) | |

(52) U.S. Cl.
CPC .......... *G06T 7/0081* (2013.01); *A61B 5/0075* (2013.01); *A61B 5/0077* (2013.01);
(Continued)

(58) Field of Classification Search
None
See application file for complete search history.

(56) References Cited

U.S. PATENT DOCUMENTS

| | | | |
|---|---|---|---|
| 8,224,425 B2 * | 7/2012 | Freeman ............. | A61B 5/0059 600/473 |
| 2010/0259651 A1 * | 10/2010 | Fattal .................... | G06T 5/003 348/241 |

(Continued)

FOREIGN PATENT DOCUMENTS

JP        2013-240175       * 11/2013   ........... G06K 9/3241

OTHER PUBLICATIONS

Achanta et al "SLIC Superpixels", EPFL Technical Report 149300, Jun. 2010.*

(Continued)

*Primary Examiner* — Siamak Harandi
*Assistant Examiner* — Mai Tran
(74) *Attorney, Agent, or Firm* — Fenwick & West LLP

(57) ABSTRACT

Embodiments segment received image data. The received image data may include pixels that have multiple channels of intensity values. The image data is decomposed into albedo and shading components. This may be accomplished using a minimization that enforces a relationship between albedo, shading, and intensity values. The minimization may also include an albedo regularizer to infer albedo in part based on chromaticity and albedo of surrounding pixels. Superpixels are generated based on contiguous regions of pixels having similar image data across channels. These superpixels are then merged based in part on the determined albedo and shading components as well as based on the image data. The channels of image data may include infrared image data used to modify visible channels of the image to create pseudo-image data, which may be used in place of image data for albedo-shading decomposition, superpixel generation, or superpixel merging.

20 Claims, 9 Drawing Sheets

(52) U.S. Cl.
CPC ............ *A61B 5/443* (2013.01); *G06T 7/0012* (2013.01); *G06T 7/408* (2013.01); *A61B 5/444* (2013.01); *A61B 2560/0475* (2013.01); *A61B 2576/00* (2013.01); *G06T 2207/10036* (2013.01); *G06T 2207/20141* (2013.01); *G06T 2207/30088* (2013.01)

(56) References Cited

U.S. PATENT DOCUMENTS

| | | | | |
|---|---|---|---|---|
| 2011/0304705 | A1* | 12/2011 | Kantor | A61B 5/0059 348/49 |
| 2014/0301637 | A1* | 10/2014 | Jin | G06T 7/408 382/162 |
| 2015/0138386 | A1* | 5/2015 | Yano | G06K 9/4642 348/222.1 |
| 2015/0332512 | A1* | 11/2015 | Siddiqui | G06T 15/80 345/633 |

OTHER PUBLICATIONS

H. Dunlop, D. R. Thompson and D. Wettergreen, "Multi-scale Features for Detection and Segmentation of Rocks in Mars Images," 2007 IEEE Conference on Computer Vision and Pattern Recognition, Minneapolis, MN, 2007, pp. 1-7. doi: 10.1109/CVPR.2007.383257.*

Achanta, R. et al., "SLIC Superpixels Compared to State-of-the-Art Superpixel Methods," IEEE Transactions Pattern Analysis and Machine Intelligence, Nov. 2012, pp. 2274-2282, vol. 34, No. 11.

Barron, J.T. et al., "Color Constancy, Intrinsic Images, and Shape Estimation," Proc. 12th European Conf. Computer Vision, 2012, pp. 57-70.

Besag, J., "On the Statistical Analysis of Dirty Pictures," Journal of the Royal Statistical Society, Series B (Methodological), 1986, pp. 259-302, vol. 48, No. 3.

Chan, T.F. et al., Active Contours Without Edges for Vector-Valued Iimages, Journal of Visual Communication and Image Representation, 2000, pp. 130-141, vol. 11.

Chen, Q. et al., "A Simple Model for Intrinsic Image Decomposition with Depth Cues," IEEE Int. Conf. Computer Vision (ICCV), Dec. 2013, 8 pages.

Cheng, L. et al., "Discriminative Segmentation of Microscopic Cellular Images," MICCAI (1), LNCS, Springer, 2011, pp. 637-644, vol. 6891.

Comaniciu, D. et al., "Mean Shift: A Robust Approach toward Feature Space Analysis," IEEE Transactions on Pattern Analysis and Machine Intelligence, May 2002, pp. 603-619, vol. 24, No. 5.

Cour, T. et al., "Spectral Segmentation with Multiscale Graph Decomposition," CVPR, IEEE Comp. Soc., 2005, pp. 1124-1131, vol. 2.

Felzenszwalb, P. et al., "Efficient Graph-Based Image Segmentation," Int'l J. Computer Vision, Sep. 2004, pp. 167-181, vol. 59, No. 2.

Funt, B.V. et al., "Recovering Shading from Color Images," Second European Conf. Computer Vision (ECCV), 1991, pp. 124-132.

Hamzavi, I. et al., "Parametric Modeling of Narrowband UV-B Phototherapy for Vitiligo Using a Novel Quantitative Tool: The Vitiligo Area Scoring Index," Arch Dermatol, 2004, pp. 677-683, vol. 140, No. 6.

Hao, Z. et al., "Learning a Structured Graphical Model with Boosted Top-Down Features for Ultra-Sound Image Segmentation," MICCAI, LNCS 8149, 2013, pp. 227-234.

Levin, A. et al., "Learning to Combine Bottom-Up and Top-Down Segmentation," Int. J. Comput. Vision, 2009, pp. 105-118, vol. 81, No. 1.

Levinshtein, A. et al., "Turbopixels: Fast Superpixels Using Geometric Flows," IEEE Trans. Pattern Analysis and Machine Intelligence, Dec. 2009, pp. 2290-2297, vol. 31, No. 12.

Mahapatra, D. et al., "Semi-Supervised and Active Learning for Automatic Segmentation of Crohns Disease," MICCAI 2013, LNCS 8150, 2013, pp. 214-221.

Moore, A. et al., "Superpixel Lattices," Proc. IEEE Conf. Computer Vision and Pattern Recognition, 2008, 8 pages.

Nadler, B. et al., "Fundamental Limitations of Spectral Clustering Methods," Schölkopf, B., et al. Eds., NIPS. MIT Press, Cambridge, MA, 2007, 8 pages.

Nguyen, X. et al., "Estimating Divergence Functionals and the Likelihood Ratio by Penalized Convex Risk Minimization," NIPS, 2007, pp. 1-8.

Shi, J. et al., "Normalized Cuts and Image Segmentation," IEEE Transactions on Pattern Analysis and Machine Intelligence, 2000, pp. 888-905, vol. 22, No. 8.

Su, P. et al., "Superpixel-Based Segmentation of Glioblastoma Multiforme from Multimodal MR Images," Multimodal Brain Image Analysis, LNCS 8159, 2013, pp. 74-83.

Taïeb, A. et al., "The Definition and Assessment of Vitiligo: a Consensus Report of the Vitiligo European Task Force," Pigment Cell Research, 2007, pp. 27-35, vol. 20, No. 1.

Tappen, M.F. et al., "Recovering Intrinsic Images from a Single Image," IEEE Trans. Pattern Analysis and Machine Intelligence, 2005, pp. 1459-1472, vol. 27, No. 9.

Veksler, O. et al., "Superpixels and Supervoxels in an Energy Optimization Framework," Proc. European Conf. Computer Vision, 2010, 14 pages.

Vese, L.A. et al., "A Multiphase Level Set Framework for Image Segmentation Using the Mumford and Shah Model," International Journal of Computer Vision, 2002, pp. 271-293, vol. 50, No. 3.

Vincent, L. et al., "Watersheds in Digital Spaces: An Efficient Algorithm Based on Immersion Simulations," IEEE Transactions on Pattern Analysis and Machine Intelligence, Jun. 1991, pp. 583-598, vol. 13, No. 6.

Wang, Q. et al., "Divergence Estimation of Continuous Distributions Based on Data-Dependent Partitions," IEEE Transactions on Information Theory, Sep. 2005, pp. 3064-3074, vol. 51, No. 9.

\* cited by examiner

SUPERPIXEL-BASED IMAGE SEGMENTATION USING SHADING AND ALBEDO DECOMPOSITION

CROSS-REFERENCE TO RELATED APPLICATION

This application claims the benefit of U.S. Provisional Application No. 62/000,255, filed May 19, 2014, which is incorporated by reference in its entirety.

BACKGROUND

Field of Disclosure

This disclosure relates generally to image processing and more particularly to image segmentation by merging superpixels based on an albedo-shading decomposition.

Description of the Related Art

Vitiligo is a de-pigmenting disorder in which progressively larger patches of skin lose their pigmentation. Studying vitiligo is complicated by lack of uniform standards to evaluate its progression. One proposed standard to evaluate vitiligo is the Vitiligo Area Scoring Index, which evaluates the progression of vitiligo in part based on extent of vitiligo (e.g., the affected surface area of skin). Regions of vitiligo are typically shaped irregularly, so measuring the area affected by vitiligo is a labor-intensive process. Accurately and efficiently measuring vitiligo would facilitate research into vitiligo treatments as well as evaluation of individuals' response to treatment. Research and treatment of other skin conditions would similarly benefit from accurate and efficient methods to measure the extent of the affected area. Although existing image processing algorithms may be used to segment medical images, these algorithms may fail to accurately and efficiently segment medical images into physiologically significant regions.

SUMMARY

Methods, systems, and computer-program products are described herein for accurately and efficiently segmenting medical images into physiologically significant regions, useful for various skin conditions for which improved methods of measuring the extent of the affected area are useful, including vitiligo. Embodiments partition an image into segmented regions that correspond to meaningfully distinct regions in the image's subject (e.g., a patient's skin). Received image data includes pixels having intensity values across different channels of the electromagnetic spectrum. The intensity values of pixels' channels are decomposed into shading and albedo components, which are used to merge superpixels into segmented regions. These generated superpixels group the pixels into contiguous regions having similar intensity values across channels. Adjacent superpixels having similar intensity values, albedo components, or shading components across channels are then successively merged until further merging would combine superpixels with significantly different intensity values across channels. The remaining superpixels are the segmented regions of pixels.

In one embodiment, pseudo-image data is created from the image data by modifying intensity values of channels intensity by values of other channels. For example, intensity values of channels of various frequencies of visible light are modified by the intensity value of a channel of a frequency of near infrared light. Albedo and shading components may be decomposed from this pseudo-image data, or from the image data. Similarly, superpixels may be generated and merged into segmented regions based on the pseudo-image data or the image data.

Embodiments include methods of segmenting image data. Embodiments include a computer-readable storage medium that stores computer-executable instructions for performing the steps described above. Embodiments include a system further comprising a processor for executing the computer-executable instructions as well as a camera or other optical sensor for recording image data.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

DETAILED DESCRIPTION

The Figures and the following description describe certain embodiments by way of illustration only. One skilled in the art will readily recognize from the following description that alternative embodiments of the structures and methods illustrated herein may be employed without departing from the principles described herein.

Reference will now be made in detail to several embodiments, examples of which are illustrated in the accompanying figures. It is noted that wherever practicable similar or like reference numbers may be used in the figures and may indicate similar or like functionality.

System Overview

Figure 1:
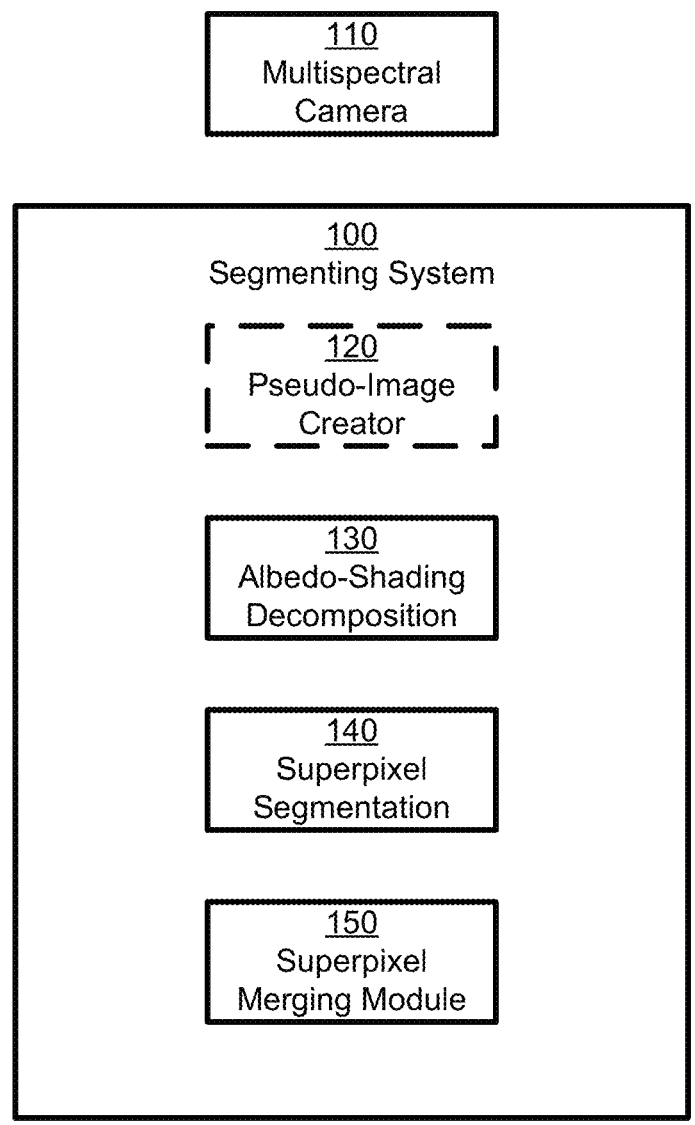
FIG. 1 is a high-level block diagram illustrating a segmenting system for segmenting image data into regions having similar color, infrared response, shading, and/or albedo, in accordance with an example embodiment.

FIG. 1 is a high-level block diagram illustrating a system for segmenting image data into regions having similar color, infrared response, shading, and/or albedo, in accordance with an example embodiment. The segmenting system 100 includes an optional pseudo-image creator 120, an albedo-shading decomposition module 130, a superpixel segmentation module 140, and a superpixel merging module 150. A multispectral camera 110 and the segmenting system 100 may be communicatively coupled over a local-area or wide-area networking using wired or wireless communication technologies. Alternatively, the multispectral camera 110 may be included as part of the segmenting system 100, e.g., communicatively coupled within a device.

The multispectral camera 110 is a camera capable of sensing light incident on an image sensor. The multispectral camera 110 may sense light over narrow and/or wide bands of light at various frequencies across the electromagnetic spectrum. In one embodiment, the multispectral camera captures visible light data measured over wide band channels and infrared light data measured over narrow band channels. For example, the visible light channels are 100 nm bandwidth channels centered at wavelengths of 650 nm, 550 nm, and 475 nm to capture RGB (red, green, blue) light; additionally, the narrowband channels measure visible and infrared light at wavelengths of 542 nm, 680 nm, 750 nm, 800 nm, and 860 nm. Hence, the multispectral camera 110 produces image data having intensity values for channels corresponding to different wavelengths of light. In one embodiment, the multispectral camera 110 produces digital image data comprising an intensity value for each channel for every pixel. Alternatively, the image data may be captured with a non-digital multispectral camera 110 and converted to digital image data.

The multispectral camera 110 may include a non-transitory storage medium such as film or a computer-readable medium (e.g., a flash memory card, an optical disc) for storing image data. The multispectral camera 110 also may include an interface device to transfer image data to the segmenting system 100 through wired or wireless means. For example, the interface device is a port for a hardware connection (e.g., via a Universal Serial Bus or an Ethernet cable), an interface for a removable non-transitory storage medium (e.g., a memory card reader, an optical disc drive), an antenna for wireless communication (e.g., via a wireless local-area network), or any other interface device suitable for this purpose. The segmenting system 100 may correspondingly include an interface device to communicate with the multispectral camera 110. Alternatively, the segmenting system 100 and the multispectral camera 110 communicate directly (e.g., via a bus) without an interface device.

Using image data captured by the multispectral camera 110, the pseudo-image creator 120 optionally creates pseudo-image data for use by the albedo-shading decomposition module 130, the superpixel segmentation module 140, or the superpixel merging module 150. To create the pseudo-image data, the pseudo-image creator 120 modifies one or more channels of the image data based on values of one or more other channels. The pseudo-image creator 120 is optional; alternatively or additionally to using pseudo-image data, the albedo-shading decomposition module 130, the superpixel segmentation module 140, or the superpixel merging module 150 use image data.

In one embodiment, the pseudo-image creator 120 modifies intensity values of RGB channels based on a function of intensity values of narrowband infrared channels. The pseudo-image data includes the modified RGB intensity values. For example, the pseudo-image creator adds or subtracts a linear combination of one or more of the infrared image channels to each of the intensity values for the R, G, and B channels. One such linear combination subtracts the intensity value for infrared light at 750 nm from the intensity value for each of the R, G, and B values. By combining visible and infrared channels of the image data, the pseudo-image data captures features of subcutaneous tissue because infrared light penetrates more deeply into the skin than visible light.

Using pseudo-image data from the pseudo-image creator 120, the albedo-shading decomposition module 130 decomposes the intensity values for the channels of the pseudo-image data into an albedo component and a shading component. These albedo and shading components of channels are used by the superpixel merging module 150. Generally, an intensity value of a channel may be decomposed into the product of an albedo component and a shading component. The albedo component is an intrinsic material property of an illuminated object that is invariant of lighting conditions and is proportional to the proportion of light reflected by a surface. The shading component reflects the lighting of an object represented by captured image data. Hence, the albedo-shading decomposition module determines an albedo component and a shading component for each channel of each pixel. The albedo-shading decomposition module 130 is described further with respect to FIG. 2 and FIG. 3.

The superpixel segmentation module 140 uses pseudo-image data from the pseudo-image creator 120 to cluster pixels into superpixels for use by the superpixel merging module 150. Typically, a superpixel is a spatially contiguous grouping of pixels having substantially similar intensity values across the channels of the pseudo-image data or image data. Grouping the pixels into superpixels increases the computational efficiency of the superpixel merging module 150, but if the superpixels contain pixels having sufficiently different intensity values, then the accuracy of the final image segmentation is compromised. For example, 150 to 250 superpixels are used to balance these two considerations.

In one embodiment, the superpixel segmentation module 140 uses the simple linear iterative clustering (SLIC) algorithm to partition the image into a desired number of superpixels containing approximately equal numbers of pixels. The SLIC algorithm seeks to minimize an objective function based on a distance metric that penalizes pixel spatial distance from the superpixel's spatial center. The distance metric also penalizes the difference between a pixel's intensity value and the mean pixel intensity value across the channels of the pixel. The SLIC algorithm includes a tunable parameter that adjusts the distance metric's relative weighting of the pixel spatial distance and the intensity value differences. For example, the tunable parameter is set to penalize the intensity value differences more than the spatial distance by a factor of 100 divided by the ratio of the total number of pixels to the number of superpixels. To increase efficiency, the SLIC algorithm may limit the search region around a pixel to a limited spatial distance from the pixel based on the desired number of pixels and a total number of pixels in the image data. The SLIC algorithm is further described by Achanta, et al., "SLIC Superpixels Compared to State-of-the-art Superpixel Methods." *IEEE Transactions on Pattern Analysis and Machine Intelligence* Vol. 34 No. 11 (November 2012) pp. 2274-82.

Using the superpixels determined by the superpixel segmentation module 140 and the albedo and shading components from the albedo-shading decomposition module 130, the superpixel merging module 150 segments the image data. To merge superpixels, the superpixel merging module 150 merges contiguous superpixels into a number of segmented regions. If fewer segmented regions are used, then the segmentation better characterizes the image data. However, merging into too few segmented regions may aggregate superpixels having dissimilar intensity values into the same segmented region and compromise the accuracy of the image segmentation. The superpixel merging module 150 is described in further detail with respect to FIG. 4.

Albedo-Shading Decomposition

Figure 2:
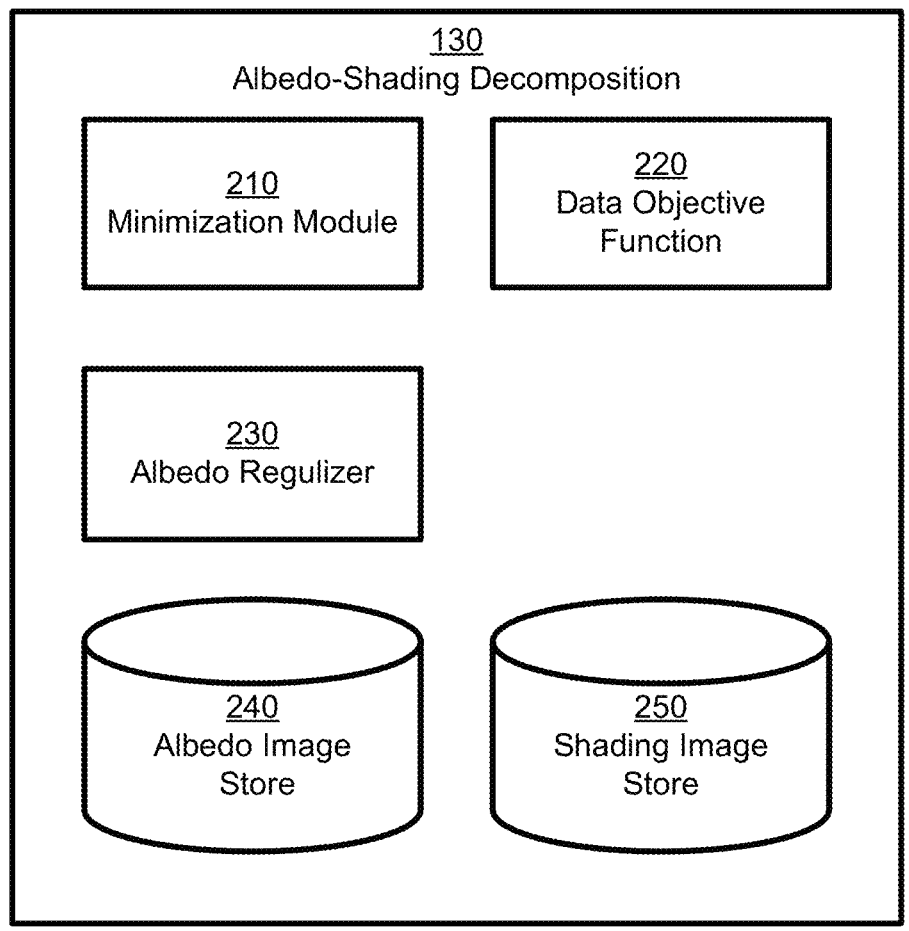
FIG. 2 is a block diagram illustrating an albedo-shading decomposition module, in accordance with an example embodiment.

FIG. 2 is a block diagram illustrating an albedo-shading decomposition module 130, in accordance with an example embodiment. The albedo-shading decomposition module 130 includes a minimization module 210, a data objective function 220, an albedo regularizer 230, an albedo image store 240, and a shading image store 250.

The minimization module 210 receives pseudo-image data from the pseudo-image creator 120 and determines albedo and shading components for each channel of each pixel. The minimization module 210 performs a minimization on an error function including a data term computed by the data objective function 220 and an albedo term computed by the albedo regularizer 230. To minimize the data term and the albedo term, the minimization module 210 varies the albedo and shading components of the image. The minimization module 210 may implement numerical optimization techniques including conjugate gradient and dynamic relaxation, for example.

In one embodiment, the minimization module 210 may vary a logarithm of the albedo and shading components because typical minimization algorithms exhibit faster and more reliable convergence when the independent variables are the same order of magnitude. After substantially minimizing the error function (at least locally) using the logarithm of the components, the minimization module 210 performs the inverse of the logarithm. To compute the error term, the minimization module 210 performs a weighted sum of the data term and the albedo term. For example, the albedo term may be weighted by a factor of 0.35 relative to the data term.

The data objective function 220 computes the data term for various values of the albedo and shading components as the minimization module 210 varies these components to substantially minimize the error function. The data objective function 220 enforces consistency between the intensity values and the computed albedo and shading components according to the product relationship between them. If the minimization module 210 varies the logarithms of the albedo and shading components of a pixel, $a_p$ and $s_p$, respectively, then for consistency with the product relationship between albedo, shading, and intensity, $i_p=a_p+s_p$, where $i_p$, is the logarithm of the intensity values of a pixel's channels.

In one embodiment, the minimization function 220 computes a difference vector for each pixel where each entry of the vector represents a channel of data for the pixel. The difference vector may be computed as $[i_p-(a_p+s_p)]$. The minimization function 220 performs a weighted sum across the magnitude squared of the difference vectors for each pixel. The difference vector may be weighted based on the luminance of the pixel $\text{lum}(I_p)$, which is the mean of the intensity values of a pixel's channels. An epsilon term (e.g., $10^{-10}$) may be added to $\text{lum}(I_p)$ to ensure that completely dark pixels have at least a threshold weight in the minimization function 220.

The albedo regularizer 230 computes the albedo term for various values of the albedo and shading components as the minimization module 210 varies these components to substantially minimize the error function. The albedo regularizer 230 regulates the albedo component of the intensity value independently of the shading component. In general, the albedo regularizer 230 enforces the assumptions that neighboring adjacent pixels have similar albedo and that pixels across the image have similar albedo. Additionally, the albedo regularizer 230 may operate on the assumption that pixels that have similar chromaticity have similar albedo. The albedo regularizer is further described with respect to FIG. 3.

The albedo image store 240 and the shading image store 250 contain the albedo and shading components for each channel of each pixel as determined by the minimization module 210.

Albedo Regularizer

Figure 3:
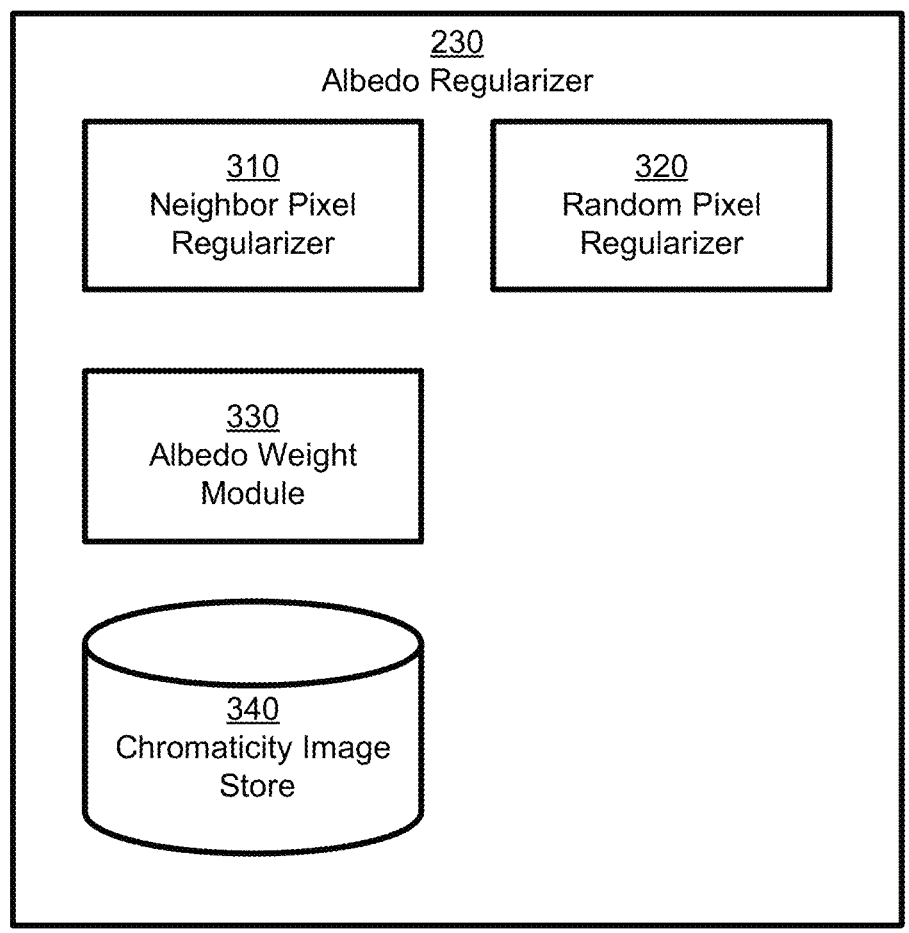
FIG. 3 is a block diagram illustrating an albedo regularizer module, in accordance with an example embodiment.

FIG. 3 is a block diagram illustrating an albedo regularizer module 230, in accordance with an example embodiment. The albedo regularizer 230 determines an albedo term for the minimization module 210 of the albedo-shading decomposition module. The albedo regularizer module 230 contains a neighbor pixel regularizer 310, a random pixel regularizer 320, an albedo weight module 330, and a chromaticity image store 340. In one embodiment, the albedo regularizer module 230 computes the albedo term from the sum of a neighbor pixel term computed by the neighbor pixel regularizer 310 and a random pixel term computed by the random pixel regularizer 320. The albedo term is this sum computed over the pixels of the pseudo-image data, and may include a weighting parameter to emphasize the neighbor pixel term or the random pixel term.

The neighbor pixel regularizer 310 computes the neighbor pixel term for a pixel based on an albedo weight from the albedo weight module 330 and the albedo components varied by the minimization module 210. The neighbor pixel regularizer may enforce the assumption in this embodiment that adjacent pixels have similar albedo values. The neighbor pixel regularizer 310 thus retrieves intensity values of pixels near to a pixel and computes the neighbor pixel term based on these retrieved neighbor pixels.

In one embodiment, the neighbor pixel regularizer 310 retrieves neighbor pixels q adjacent to a pixel p and computes albedo comparisons between the pixel p and each of its retrieved neighbor pixels q. Pixels "adjacent" to a pixel p include pixels that horizontally, vertically, or diagonally border the pixel p. In an alternative embodiment, neighbor pixels q of a pixel p are within a threshold distance (e.g., Cartesian distance, Manhattan distance) of pixel p. The albedo comparison may be the magnitude of a difference vector $[a_p-a_q]$ between the albedo components of the pixels, where $a_p$ and $a_q$ are the albedo components across the channels of the p and q pixels respectively. The magnitude of the difference vector is squared and added to a weighted sum for the pixel p. The sum may be weighted based on an albedo weight $\alpha_{pq}$ computed between the pixel p and each adjacent pixel q by the albedo weight module 330.

The random pixel regularizer 320 computes the random pixel term for a pixel based on an albedo weight from the albedo weight module 330 and the albedo components varied by the minimization module 210. The random pixel regularizer 320 generally enforces the assumption that pixels across the image have similar albedo values. The random pixel regularizer 320 thus retrieves intensity values of pixels randomly selected from the image and computes the random pixel term based on these retrieved random pixels.

In one embodiment, the random pixel regularizer 320 randomly selects random pixels q from across the image and computes a pairwise albedo comparison between each of the randomly selected pixels q and a pixel p. The albedo comparison may be the magnitude of a difference vector $[a_p-a_q]$ between the albedo components of the pixels, where $a_p$ and $a_q$ are the albedo components across the channels of the p and q pixels respectively. The magnitude of the difference vector is squared and added to a weighted sum for the pixel p. The sum may be weighted based on an albedo weight $\alpha_{pq}$ computed between the pixel p and each adjacent pixel q by the albedo weight module 330.

The optional chromaticity image store 340 contains a chromaticity image of the pseudo-image data, which may be computed by normalizing the intensity value for each channel of a pixel by the sum of the intensity values for that pixel's channels. In one embodiment, the albedo weight module 330 uses the chromaticity image store 340.

The albedo weight module 330 computes an albedo weight between two pixels to weight albedo differences computed by the neighbor pixel regularizer 310 and the random pixel regularizer 320. The albedo weight is computed based on the chromaticity image from the chromaticity image store 340 and based on the luminance values of the two pixels. The computed albedo weight is typically higher when the two pixels have similar chromaticity values because pixels with similar chromaticity tend to have similar albedo. Higher luminance values for the two pixels also receive higher weights to diminish the weight of dark pixels.

In one embodiment, the albedo weight module 330 computes the albedo weight as a product of a chromaticity similarity factor and a luminance factor. The chromaticity similarity factor may be computed from $$\left(1 - \frac{\|ch_p - ch_q\|}{\max\_ch(p)}\right),$$

where $ch_p$ and $ch_q$ are the chromaticity of the pixels p and q, respectively, and $\max\_ch(p)$ is the maximum magnitude of chromaticity difference vectors between pixel p and its neighbor pixels. The luminance factor may be computed from $\sqrt{\mathrm{lum}(I_p)\mathrm{lum}(I_q)}$, the geometric mean of the luminances $\mathrm{lum}(I_p)$ and $\mathrm{lum}(I_q)$ of pixels p and q respectively.

Superpixel Merging

Figure 4:
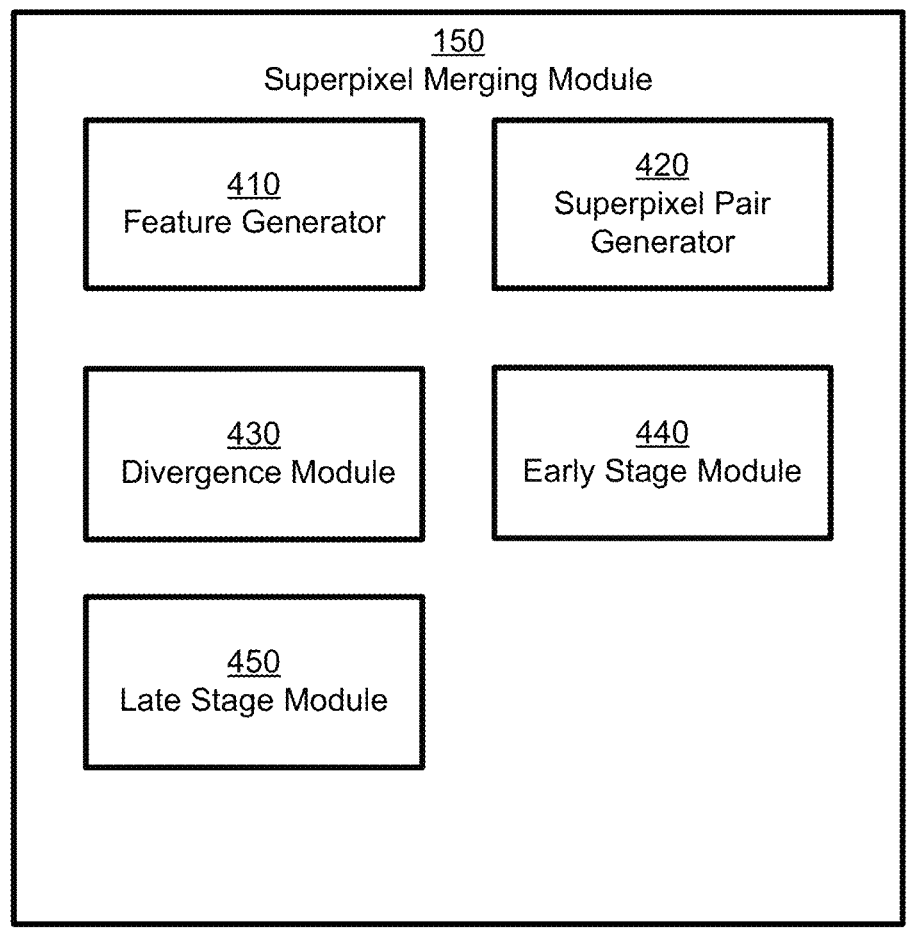
FIG. 4 is a block diagram illustrating a superpixel merging module, in accordance with an example embodiment.

FIG. 4 is a block diagram illustrating a superpixel merging module 150, in accordance with an example embodiment. The superpixel merging module 150 merges superpixels generated by the superpixel segmentation module 140 based on pseudo-image data from the pseudo-image creator 120 and the albedo and shading components determined by the albedo-shading decomposition module 130. Superpixels are merged into a segmented region, each of which contains the pixels of the superpixels merged to create that segmented region. The superpixel merging module 150 includes a feature generator 410, a superpixel pair generator 420, a divergence module 430, an early stage module 440, and a late stage module 450.

The early stage module 440 initially controls superpixel merging by selecting superpixel pairs (from the superpixel pair generator 420) to merge based on a dissimilarity metric (from the divergence module 430). The merged superpixels are stored as segmented regions. In one embodiment, the early stage module 440 iteratively receives superpixel pairs, ranks them according to a dissimilarity metric, and selects the most similar pair (based on the distance metric) for merging. The superpixel pair generator 420 removes the superpixel pair containing the merged superpixels and generates new pairs of superpixels including the newly merged superpixel. The divergence module 430 calculates dissimilarity metrics for the newly generated superpixels, and the early stage module 440 again ranks superpixel pairs and selects a pair for merging.

The early stage module 440 continues merging superpixels until one or more conditions are met, and then a late stage module 450 that applies more stringent conditions for merging superpixels may optionally complete superpixel merging. These conditions on merging prevent merging of superpixels from regions of the image corresponding to different ground truths (e.g., regions that represent meaningfully different regions of the image's subject). In one embodiment, the early stage module 440 may stop merging superpixels if a threshold number of superpixels (including both unmerged and merged superpixels) remain. For example, the early stage module 440 stops merging superpixels when a predetermined number of superpixels remain, e.g., when 10 superpixels remain. However, the number of meaningful regions in the image (in other words, the ideal number of segmented regions) is typically unknown, so other conditions may be implemented.

The early stage module 440 may stop merging superpixels based on the dissimilarity metric. For example, the early stage module 440 predicts the dissimilarity metric for the next pair of superpixels selected for merging. If the dissimilarity metric of the superpixel pair is greater, by a threshold, than the predicted dissimilarity metric, the early stage module 440 stops merging superpixels. The predicted distance metric may be determined from a regression of the distance metrics of previously merged pairs of superpixels.

The superpixel pair generator 420 creates pairs between remaining superpixels based on the spatial properties of superpixels determined by the superpixel segmentation modules 140. The generated pairs of superpixels are ranked and merged by the early and late stage module 440 and 450. In one embodiment, the superpixel pair generator 420 generates pairs of adjacent superpixels for merging to ensure that merged superpixels become a contiguous superpixel.

To determine the dissimilarity metric for a pair of superpixels (as used by the early and late stage modules 440 and 450), the divergence module 430 uses a feature set determined by the feature generator 410. Generally, the divergence module 430 determines one or more representative quantities for a superpixel based on the feature set of each pixel in the superpixel. The divergence module 430 compares the one or more representative quantities for each superpixel to determine the dissimilarity metric.

In one embodiment, the divergence module 430 uses the symmetric version of the Kullback-Leibler (KL) divergence. To implement the KL divergence, the divergence module 430 may represent the feature set of a pixel as a vector and compute a mean vector for each of the compared superpixels as well as a covariance matrix for each of the compared superpixels. Using the mean vector and covariance matrix of each superpixel as representative features, the divergence module 430 computes the dissimilarity metric according to the symmetric version of the KL divergence. The symmetric KL divergence may be computed from $$\frac{1}{2}\left(tr(\Sigma_1^{-1}\Sigma_0) + (\mu_1 - \mu_0)^T\Sigma_1^{-1}(\mu_1 - \mu_0) - d - \log\left|\frac{\Sigma_0}{\Sigma_1}\right|\right),$$

where $\Sigma_0$, and $\Sigma_1$ are covariance matrices of intensity values of the channels of a first superpixel and a second superpixel, respectively, $\mu_1$ and $\mu_0$ are mean vectors of intensity values of the channels of the first and second superpixels, respectively, and d is the feature dimension (e.g., the number of features used). This version of the KL divergence may be computed with matrix operations including the trace, transpose, inverse, determinant, and matrix product.

To generate the feature sets used by the divergence module 430 to calculate a dissimilarity metric, the feature generator 410 determines features for a pixel from the pixel's image data, pseudo-image data (from the pseudo-image creator 120), albedo and shading components (from the albedo-shading decomposition module 130), or a combination thereof. In one embodiment, the generated feature set includes features based on the pseudo-color image from the formula $RGB_{pseudo}*(1+\gamma S)$, where $RGB_{pseudo}$ corresponds to a channel of the pseudo-image, $\gamma$ is a tunable parameter, and S is the shading component corresponding to the channel of the pseudo-image. Similarly, the generated features include features based on the image data from the formula $\alpha RGB*(1+\gamma S)$, where RGB corresponds to a channel of the image data and $\alpha$ is a tunable parameter. The generated features may also include features based on the albedo image from the formula $\beta A*(1+\gamma S)$, where A is the albedo component corresponding to the shading component and $\beta$ is a tunable parameter. Lastly, the generated features may include a feature based on overall brightness of the image (e.g., luminance, luma) and another tunable parameter $\kappa$. Example values of the tunable parameters $\alpha$, $\beta$, $\gamma$, and $\kappa$ are 0.3, 0.1, 0.1, and 0.5, respectively.

The late stage module 450 merges remaining superpixels after the early stage module 440 stops merging superpixels. Similar to the early stage module 440, the late stage module 450 may rank pairs of remaining superpixels by a dissimilarity metric and select a pair of superpixels having the lowest divergence metric out of the ranked pairs for merging. In contrast to the early stage module 440, the late stage module 450 may apply more stringent conditions for merging superpixels. For example, the late stage module 450 enforces a minimum threshold on the dissimilarity metric. If a pair of superpixels has a higher dissimilarity metric than the threshold, the late stage module 450 does not merge the superpixels in the pair.

In one embodiment, the divergence module 430 determines an alternative or additional dissimilarity metric for use by the late stage module 450. For example, the divergence module determines a dissimilarity metric based on the feature sets of pixels at or near a common boundary of the pair of superpixels. The dissimilarity metric may be based on the standard deviation or mean of the feature sets of the boundary pixels. Boundary pixels of a superpixel with respect to another superpixel include those pixels on the border of the superpixel that are adjacent to the other superpixel. For example, when computing the dissimilarity metric between two superpixels, the late stage module 450 computes the mean and standard deviation of feature values of boundary pixels for the first superpixel, where the boundary pixels are adjacent to the second superpixel. Continuing the example, late stage module 450 calculates the mean and standard deviation of feature values of boundary pixels for the second superpixel, where the boundary superpixels are adjacent to the first superpixel. In the example, the late stage module 450 uses as a dissimilarity metric a comparison of the computed means and standard deviations of both sets of boundary pixels.

In one embodiment, the feature generator 410 determines an alternative or additional feature to determine the dissimilarity metric by the divergence module 430 for use by the late stage module 450. The feature may include a feature that is a linear combination of the shading component determined by the albedo-shading decomposition module 130 and the luminance (or some other representation of a pixel's brightness such as luma). For example, the feature is determined from $(1-\eta)\overline{S}+\eta L$, where $\eta$ is a tunable parameter, $\overline{S}$ is the average shading component across channels, and L is the luminance. An example value of $\eta$ is 0.8.

Computer System

Figure 5:
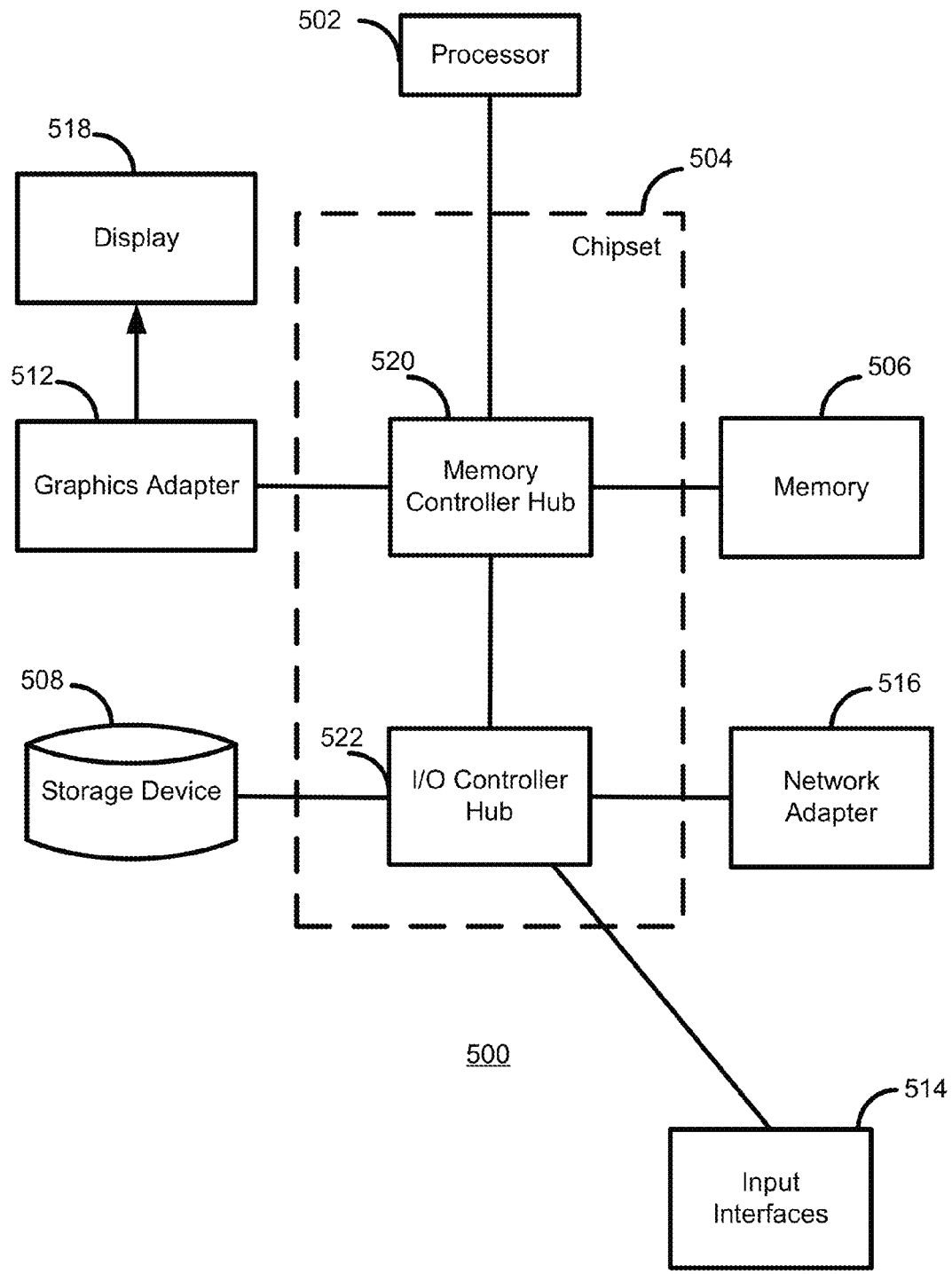
FIG. 5 is a block diagram illustrating an example computer for implementing components of the segmenting system shown in FIG. 1, in accordance with an example embodiment.

FIG. 5 is a block diagram illustrating an example computer 500 for implementing components of the segmenting system 100 shown in FIG. 1, in accordance with an example embodiment. The computer 500 includes at least one processor 502 coupled to a chipset 504. The chipset 504 includes a memory controller hub 520 and an input/output (I/O) controller hub 522. A memory 506 and a graphics adapter 512 are coupled to the memory controller hub 520, and a display 518 is coupled to the graphics adapter 512. A storage device 508, input interfaces 514, and network adapter 516 are coupled to the I/O controller hub 522. Other embodiments of the computer 500 have different architectures (e.g., an embedded system to implement the segmenting system 100, a cloud-based server system).

The storage device 508 is a non-transitory computer-readable storage medium such as a hard drive, compact disk read-only memory (CD-ROM), DVD, or a solid-state memory device. Non-transitory computer-readable media include computer-readable media with the exception of a transitory, propagating signal. The memory 506 holds instructions and data used by the processor 502. The input interfaces 514 may include a touch-screen interface, a mouse, track ball, or other type of pointing device, a keyboard, a camera, or some combination thereof, and is used to input data, including image data, into the computer 500. The graphics adapter 512 displays images and other information on the display 518. The network adapter 516 couples the computer 500 to one or more computer networks.

The computer 500 is adapted to execute computer program modules for providing functionality described herein. As used herein, the term "module" refers to computer program logic used to provide the specified functionality. Thus, a module can be implemented in hardware, firmware, and/or software. In one embodiment, program modules (e.g., pseudo-image creator 120, albedo-shading decomposition module 130, superpixel segmentation module 140, superpixel merging module 150) are stored on the storage device 508, loaded into the memory 506, and executed by the processor 502.

The type of computer 500 used for segmenting system 100 can vary depending upon the embodiment. For example, the segmenting system 100 may include multiple computers 500 communicating with each other through a network to provide the functionality described herein. Such computers 500 may lack some of the components described above, such as graphics adapters 512 and displays 518. Alternatively or additionally, the multispectral camera 110 and at least some components of the computer 500 implementing the segmenting system 100 are integrated as a single device, such as a camera.

Segmenting Images into Regions

Figure 6:
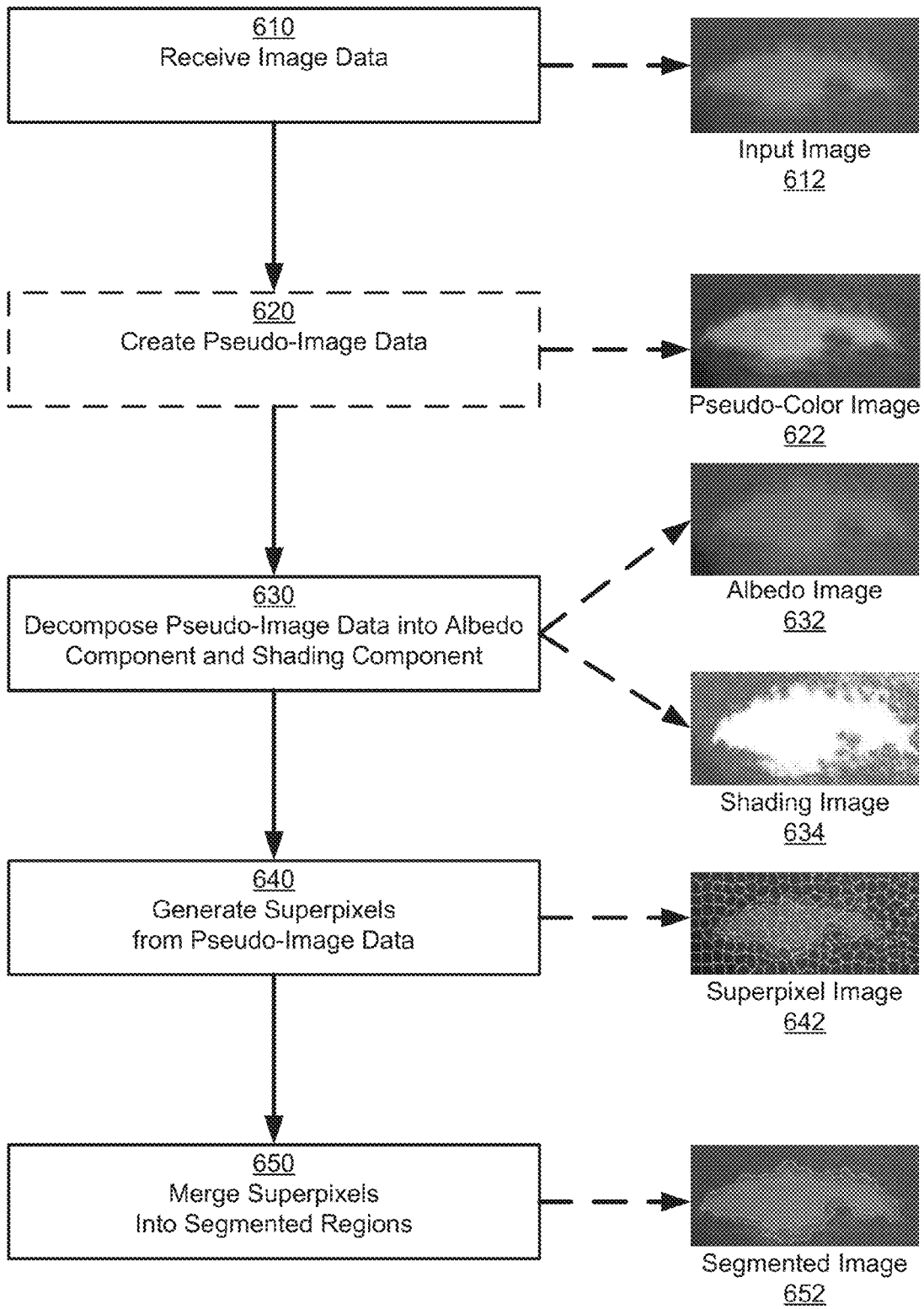
FIG. 6 is a flowchart illustrating a method for segmenting image into regions, in accordance with an example embodiment.

FIG. 6 is a flowchart illustrating a method for segmenting an image into regions, in accordance with an example embodiment. A segmenting system (e.g., segmenting system 100 of FIG. 1) receives 610 image data (e.g., from the multispectral camera 110), each pixel of the image data having intensity values for a channel representing light sensed from a different band of light frequency. The illustrated input image 612 is an example of the visible light channels (e.g., RGB) of received image data. The system optionally creates 620 a pseudo-image having pseudo-image channels based on the intensity values of the image data's channels. The pseudo-color image 622 illustrates the visible light channels of the example input image 612 after modification based on an infrared light channel. In one embodiment, creating 620 the pseudo-image is performed by the pseudo-image creator 120 described in conjunction with FIG. 1.

The system decomposes 630 the pseudo-image data into albedo and shading components based on the pseudo-image channels of the pseudo-image. Decomposing the pseudo-image data into albedo and shading components is described further with respect to FIG. 7 and FIG. 8. The albedo image 632 and the shading image 634 illustrate the albedo components and shading components of the channels of the pseudo-color image 622. In an alternative embodiment, the system decomposes image data into albedo and shading components instead of decomposing pseudo-image data. In one embodiment, decomposing 630 pseudo-image data or image data into albedo components and shading components is performed by the albedo-shading decomposition module 130 described in conjunction with FIGS. 2 and 3. The system generates 640 superpixels from the created pseudo-image data or the image data. Each superpixel contains contiguous pixels having similar values in their pseudo-image channels or image channels. The superpixel image 642 illustrates superpixel boundaries overlaid over the input image 612. In one embodiment, generating 640 the superpixels is performed by the superpixel segmentation module 140 described in conjunction with FIG. 1. The system merges 650 the generated superpixels into segmented regions based at least in part on one or more of the pseudo-image data or the image data. These segmented regions contain contiguous merged superpixels. Merging superpixels into segmented regions in described further with respect to FIG. 9. The segmented image 652 illustrates the boundaries of the segmented regions overlaid over the input image 612. In one embodiment, merging 650 the superpixels is performed by the superpixel merging module 150 described in conjunction with FIG. 4.

Decomposing Image Data into Albedo and Shading Components

Figure 7:
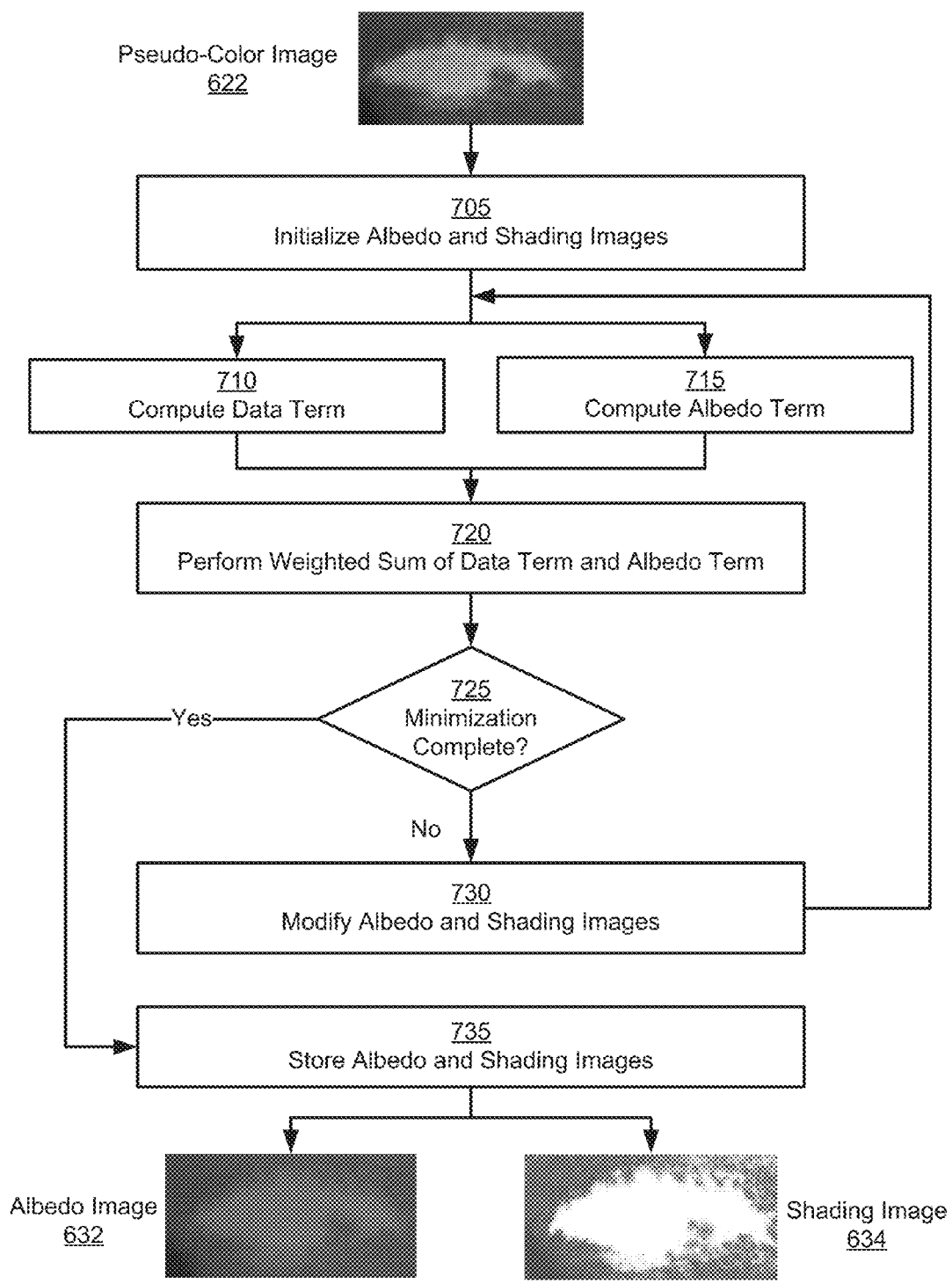
FIG. 7 is a flowchart illustrating a method of decomposing image data into albedo and shading components, in accordance with an example embodiment.

FIG. 7 is a flowchart illustrating a method of decomposing image data into albedo and shading components, in accordance with an example embodiment. The system (e.g., segmenting system 100 of FIG. 1) receives pseudo-image data (such as the example pseudo-color image 622) or image data. The system initializes 705 the albedo and shading images. Initialization generally varies with the minimization technique used, and may involve random number generation, some heuristic based on the image data, or a combination thereof. In one embodiment, initializing 705 the albedo and shading images is performed by the minimization module 210 described in conjunction with FIG. 2. The system computes 710 a data term, and the system computes 715 an albedo term. Computing 715 the albedo term is described in further detail with respect to FIG. 8. In one embodiment, computing 710 the data term is performed by the data objective function 220 described in conjunction with FIG. 2, and computing 715 the albedo term is performed by the albedo regularizer 230 described in conjunction with FIGS. 2 and 3. The computed albedo term and data term are combined when the system performs 720 a weighted sum of these two terms to determine a measure of error. In one embodiment, performing 720 the weighted sum is done by the minimization module 210 described in conjunction with FIG. 2.

The system determines whether 725 the minimization is complete, which depends on the minimization algorithm used (e.g., a threshold number of iterations, a threshold value of the error term, a threshold change in the error term between iterations). In one embodiment, determining whether 725 the minimization is complete is performed by the minimization module 210 described with respect to FIG. 2. If 725 the minimization is complete, the system stores 735 the albedo and shading images 632 and 634. In one embodiment, the albedo and shading images 632 and 634 are stored 735 in the albedo and shading image stores 240 and 250 described in conjunction with FIG. 2. If 725 the minimization is not complete, the system modifies 730 the albedo and shading components and begins another iteration starting with computing 710 the data term and computing 715 and the albedo term. In one embodiment, modifying 730 the albedo and shading components is performed by the minimization module 210 described in conjunction with FIG. 2.

Regularizing Albedo in a Minimization to Decompose Image Data

Figure 8:
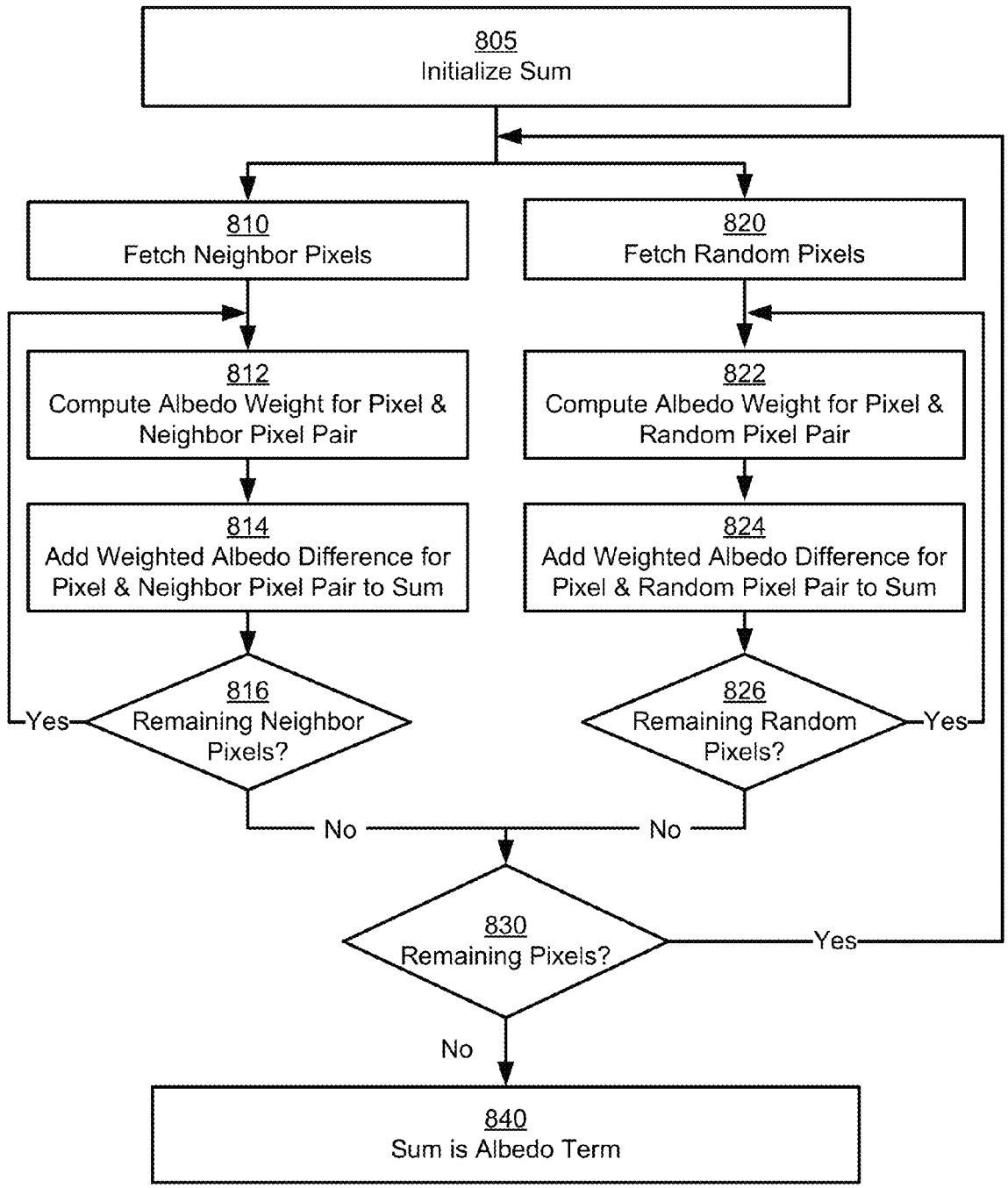
FIG. 8 is a flowchart illustrating a method of regularizing albedo in a minimization to decompose image data into albedo and shading components.

FIG. 8 is a flowchart illustrating a method of regularizing albedo in a minimization to decompose image data into albedo and shading components. The system (e.g., segmenting system 100 of FIG. 1) initializes 805 a sum (which is the albedo term) to zero and begins calculating a neighbor pixel term and a random pixel term for each pixel of the image data or pseudo-image data. In one embodiment, initializing 805 the sum is performed by the albedo regularizer 230 described in conjunction with FIGS. 2 and 3.

To compute the neighbor pixel term for a pixel, the system fetches 810 a pixel's neighbor pixels, which are adjacent to the pixel or within a threshold distance of the pixel. For each of the neighbor pixels, the system computes 812 an albedo weight between the pixel and the pixel's neighbor pixel. In one embodiment, computing 812 the albedo weight is performed by the albedo weight module 330 described in conjunction with FIG. 3. Using this albedo weight, the system adds 814 a weighted albedo difference between the pixel and the neighbor pixel to the sum. The system determines whether 816 there are remaining neighbor pixels. If 816 there are remaining neighbor pixels, then an albedo weight and a weighted albedo difference are calculated for each of those remaining neighbor pixels. In one embodiment, fetching 810 the neighbor pixels, adding 814 the weighted albedo difference, and determining whether 816 there are remaining neighbor pixels are performed by the neighbor pixel regularizer 310 described in conjunction with FIG. 3.

To compute the random pixel term for a pixel, the system fetches 820 a set of random pixels, which are generally more than a minimum threshold distance but less than a maximum threshold difference from the pixel. For each of the random pixels, the system computes 822 an albedo weight between the pixel and the random pixel. Computing 822 the albedo weight may be performed by the albedo weight module 330 described in conjunction with FIG. 3. Using this albedo weight, the system adds 824 a weighted albedo difference between the pixel and the random pixel to the sum. The system determines whether 826 there are remaining random pixels. If 826 there are remaining random pixels, then an albedo weight and a weighted albedo difference are calculated for each of those remaining random pixels. In one embodiment, fetching 820 the random pixels, adding 824 the weighted albedo difference to the sum, and determining whether 826 there are remaining random pixels are performed by the random pixel regularizer 320 described in conjunction with FIG. 3.

If 816 there are no remaining neighbor pixels, and if 826 there are no remaining random pixels, then the pixel's contribution has been added to the albedo term. The system then determines whether 830 there are other remaining pixels unaccounted for in the albedo term. In one embodiment, determining whether 830 there are remaining pixels is performed by the albedo regularizer 230 described in conjunction with FIG. 3. If 830 there remaining pixels, then the system fetches 810 neighbor pixels to an additional pixel, and also the system fetches 820 random pixels to the additional pixel. If 830 there are no remaining pixels, then the resulting sum is 840 the albedo term. In other words, the albedo term is a sum of each pixel's contribution to the albedo term.

Merging Superpixels

Figure 9:
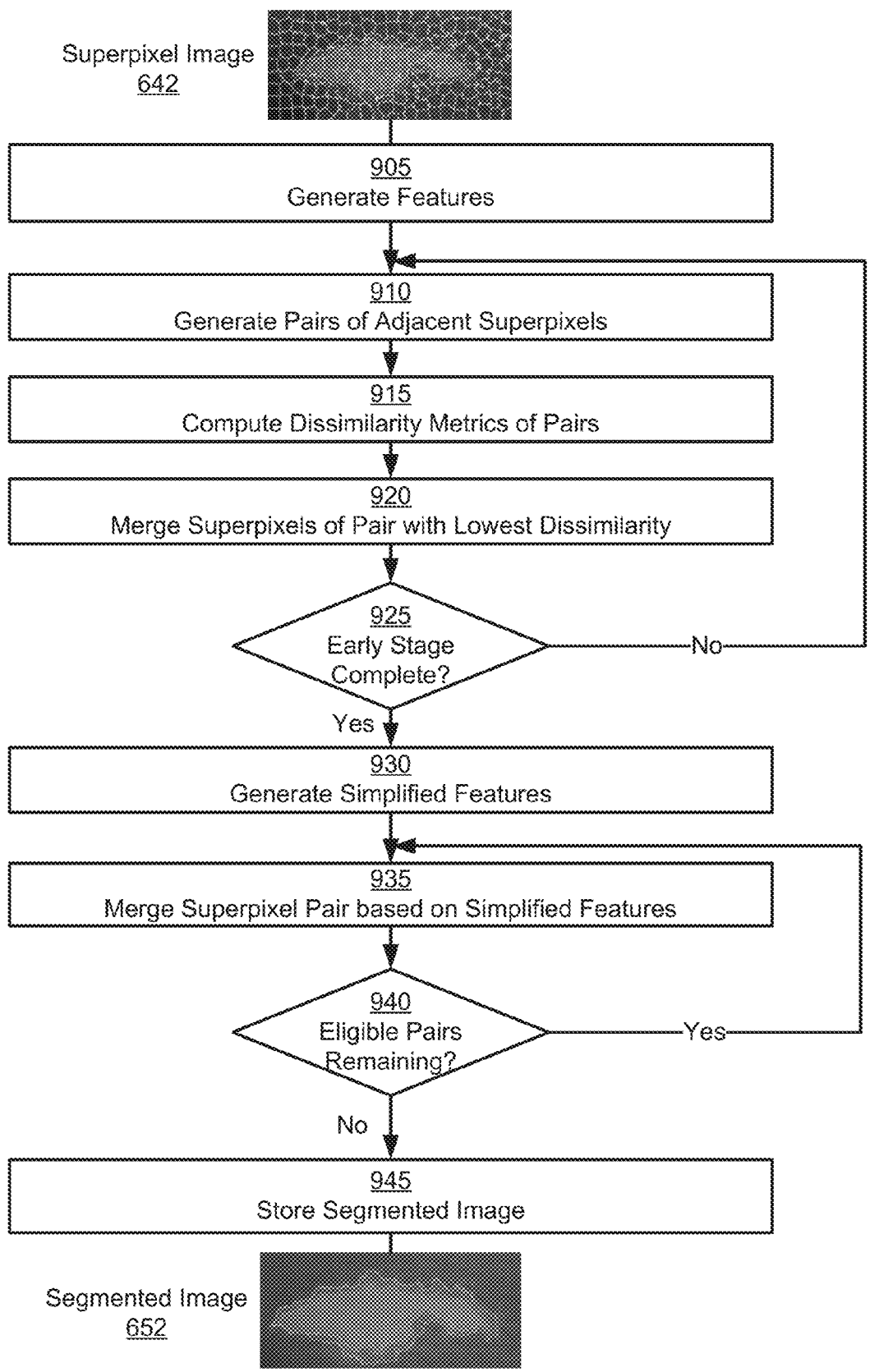
FIG. 9 is a flowchart illustrating a method for merging superpixels to segment image data, in accordance with an example embodiment.

FIG. 9 is a flowchart illustrating a method for merging superpixels to segment image data, in accordance with an example embodiment. The system (e.g., segmenting system 100 of FIG. 1) receives the superpixel image 642 and generates 905 features for each superpixel based on the channels of the pseudo-image data or the channels of the image data. In one embodiment, generating 905 the features is performed by the feature generator 410 described in conjunction with FIG. 4. The system generates 910 pairs of adjacent superpixels, and the system computes 915 dissimilarity metrics between the pixels in each pair. In one embodiment, generating 910 the pairs of adjacent superpixels is performed by the superpixel pair generator 420 described in conjunction with FIG. 4, and computing 915 dissimilarity metrics is performed by the divergence module 430 described in conjunction with FIG. 4. The system merges 920 the superpixels of the pair with the lowest dissimilarity metric (or alternatively with a maximum similarity metric). The system determines whether 925 an early stage is complete based on one or more conditional tests relating to a remaining number of superpixels or the dissimilarity metric, for example. If 925 the early stage is not complete, then the system continues merging superpixels, starting with generating 910 pairs of adjacent superpixels to reflect the merged superpixels. In one embodiment, merging 920 the superpixels and determining whether 925 the early stage is complete are performed by the early stage module 440 described in conjunction with FIG. 4.

If 925 the early stage is complete, then the system generates 930 simplified features for use in the late stage. In one embodiment, generating 930 the simplified features is performed by the feature generator 410 described in conjunction with FIG. 4. The system merges 935 superpixels in a pair based at least in part on the simplified features, which may include alternative or additional dissimilarity measures computed by the system. In this late stage, the system determines whether 940 there are pairs of superpixels eligible for merging based on criteria that are typically more stringent than those used in the early stage. If 940 there are eligible pairs of superpixels remaining, then the system continues merging 935 pairs of superpixels. If 940 there are no eligible pairs of superpixels remaining, then the late stage is complete, and the system stores 945 the segmented image 652. In one embodiment, merging 935 the superpixels, determining whether 940 eligible pairs of superpixels are remaining, and storing 945 the segmented image are performed by the late stage module 450 described in conjunction with FIG. 4

Additional Considerations

The methods and systems disclosed herein may use image data from the multispectral camera 110, pseudo-image data from the pseudo-image creator 120, or a combination thereof. In particular, the albedo-shading decomposition module 130, the superpixel segmentation module 140, and the superpixel merging module 150 may operate on image data, pseudo-image data, or a combination thereof. Hence, references to "image data" or "pseudo-image data" with respect to these modules 130, 140, or 150 or their component modules should be understood to refer to image data, pseudo-image data, or a combination thereof unless an explicit distinction is made.

Some portions of the above description describe the embodiments in terms of algorithmic processes or operations. These algorithmic descriptions and representations are commonly used by those skilled in the data processing arts to convey the substance of their work effectively to others skilled in the art. These operations, while described functionally, computationally, or logically, are understood to be implemented by computer programs comprising instructions for execution by a processor or equivalent electrical circuits, microcode, or the like. The operations described herein may be performed using on or more suitable data structures. For example, data may be stored as arrays, lists, hash tables, trees, stacks, or heaps. In one embodiment, image data is stored in a two-dimensional array of data cells where a cell's row and column correspond to a pixel's location in the image and the data value in the data cell corresponds to an intensity value of the pixel. Other data that may be stored in a two-dimensional array include pseudo-image data, albedo components, shading components, or chromaticity values of an image. Furthermore, it has also proven convenient at times, to refer to these arrangements of functional operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the disclosure. This description should be read to include one or at least one and the singular also includes the plural unless it is obvious that it is meant otherwise.

Upon reading this disclosure, those of skill in the art will appreciate still additional alternative structural and functional designs. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the method and apparatus disclosed herein.

What is claimed is:

1. A method comprising:
   receiving image data comprising pixels, each pixel associated with one or more image channels of image data;
   decomposing, by a processor, each image channel of the image data into an albedo component and a shading component based on the one or more image channels;
   generating superpixels from the created image data, each superpixel comprising a plurality of contiguous image pixels having similar values in corresponding image channels, the albedo component invariant of lighting conditions and proportional to a proportion of light reflected by a surface represented in the image data; and
   merging the generated superpixels into segmented regions based at least in part on the albedo component and the shading component of each image channel, each segmented region comprising image pixels of contiguous merged superpixels.

2. The method of claim 1, wherein decomposing each image channel into the albedo component and the shading component comprises:
   determining the albedo component and the shading component of each image channel by substantially minimizing a measure of error between values of each image channel and the albedo component and the shading component of each channel.

3. The method of claim 2, wherein the measure of error includes an albedo term, and wherein computing the albedo term comprises:
   for each pixel of the received image:
      selecting a random plurality of nonadjacent pixels;
      performing a weighted sum based on a difference between albedo components of each pixel and of the selected nonadjacent pixels; and
   summing the weighted sum for each pixel to compute the albedo term.

4. The method of claim 3, wherein performing the weighted sum comprises:
   determining an albedo weight for each selected nonadjacent pixel based on a difference between chromaticity values of the selected nonadjacent image pixel and of each image pixel.

5. The method of claim 1, wherein merging the generated superpixels into segmented regions comprises:
   generating a feature set based at least in part on the one or more image channels, the albedo component, and the shading component;
   computing a dissimilarity metric between adjacent pairs of superpixels based on the generated feature set; and
   merging adjacent superpixels based on the computed dissimilarity metric between the adjacent pairs of superpixels.

6. The method of claim 5, wherein merging adjacent superpixels based on the computed dissimilarity metric comprises:
   selecting a pair of adjacent superpixels having a minimum dissimilarity metric for merging;
   comparing the minimum dissimilarity metric to a predicted minimum dissimilarity metric determined based on dissimilarity metrics of previously merged pairs of superpixels; and
   halting the merging of adjacent superpixels in response to the minimum dissimilarity metric being greater than the predicted minimum dissimilarity metric by a threshold.

7. A method comprising:
   receiving image data comprising pixels, each pixel associated with one or more channels of image data;
   creating pseudo-image data comprising pseudo-image pixels based on the one or more channels of the image data, each pseudo-image pixel associated with one or more pseudo-image channels;
   decomposing, by a processor, each pseudo-image channel of the created pseudo-image data into an albedo component and a shading component based on the one or more pseudo-image channels, wherein the albedo component is invariant of lighting conditions and proportional to a proportion of light reflected by a surface represented in the image data;
   generating superpixels from the created pseudo-image data, each superpixel comprising a plurality of contiguous pseudo-image pixels having similar values in corresponding pseudo-mage channels; and
   merging the generated superpixels into segmented regions based at least in part on the albedo component and the shading component of each pseudo-image channel, each segmented region comprising pseudo-image pixels of contiguous merged superpixels.

8. The method of claim 7, wherein the one or more channels of image data comprise visible light channels and one or more infrared light channels.

9. The method of claim 8, wherein creating the pseudo-image data comprises:
   modifying each of the visible light channels based on a function of the one or more infrared light channels to determine the one or more pseudo-image channels.

10. The method of claim 7, wherein decomposing each pseudo-image channel into the albedo component and the shading component comprises:
    determining the albedo component and the shading component of each pseudo-image channel by substantially minimizing a measure of error between values of each pseudo-image channel and the albedo component and the shading component of each channel.

11. The method of claim 10, wherein determining the albedo component and the shading component of each pseudo-image channel by substantially minimizing the measure of error comprises:
    computing the measure of error based on logarithms of the values of each pseudo-image channel, the albedo component of each channel, and the shading component of each channel.

12. The method of claim 10, wherein the measure of error includes an albedo term, and wherein computing the albedo term comprises:
    for each pseudo-image pixel:
       selecting a random plurality of nonadjacent pseudo-image pixels;
       performing a weighted sum based on a difference between albedo components of each pseudo-image pixel and of the selected nonadjacent pseudo-image pixels; and
    summing the weighted sum for each pseudo-image pixel to compute the albedo term.

13. The method of claim 12, wherein performing the weighted sum comprises:
   determining an albedo weight for each selected nonadjacent pseudo-image pixel based on a difference between chromaticity values of the selected nonadjacent pseudo-image pixel and of each pseudo-image pixel.

14. The method of claim 7, wherein merging the generated superpixels into segmented regions comprises:
   generating a feature set based at least in part on the one or more pseudo-image channels, the albedo component, and the shading component;
   computing a Kullback-Leibler divergence between adjacent pairs of superpixels based on the generated feature set; and
   merging adjacent superpixels based on the computed Kullback-Leibler divergence between the adjacent pairs of superpixels.

15. The method of claim 14, wherein merging adjacent superpixels based on the computed Kullback-Leibler divergence comprises:
   selecting a pair of adjacent superpixels having a minimum Kullback-Leibler divergence for merging;
   comparing the minimum Kullback-Leibler divergence to a predicted minimum divergence determined based on divergences of previously merged pairs of superpixels; and
   halting the merging of adjacent superpixels in response to the minimum Kullback-Leibler divergence being greater than the predicted minimum divergence by a threshold.

16. A system comprising:
   a processor; and
   a non-transitory, computer-readable storage medium storing instructions executable by the processor, the instructions comprising instructions for:
      decomposing image data into shading components and albedo components, the image data containing pixels, each pixel associated with one or more image channels, each image channel of image data decomposed into an albedo component and a shading component;
      generating superpixels from the created image data, each superpixel comprising a plurality of contiguous image pixels having similar values in corresponding image channels, the albedo component invariant of lighting conditions and proportional to a proportion of light reflected by a surface represented in the image data; and
      merging the generated superpixels into segmented regions based at least in part on the albedo component and the shading component of each image channel, each segmented region comprising image pixels of contiguous merged superpixels.

17. The system of claim 16, further comprising:
   a camera to capture the image data.

18. The system of claim 16, wherein the channels of image data comprise visible light channels and one or more infrared light channels, and wherein the storage medium further comprises instructions for:
   creating pseudo-image data comprising pseudo-image pixels by modifying each of the visible light channels based on a function of the one or more infrared light channels to determine pseudo-image channels associated with each pseudo-image pixel.

19. The system of claim 16, wherein decomposing each image channel into the albedo component and the shading component comprises:
   determining the albedo component and the shading component of each image channel by substantially minimizing a measure of error between values of each image channel and the albedo component and the shading component of each channel.

20. The system of claim 16, wherein merging the generated superpixels into segmented regions comprises:
   generating a feature set based at least in part on the one or more image channels, the albedo component, and the shading component;
   computing a dissimilarity metric between adjacent pairs of superpixels based on the generated feature set; and
   merging adjacent superpixels based on the computed dissimilarity metric between the adjacent pairs of superpixels.

* * * * *